United States Patent [19]

Solomon

[11] Patent Number: 4,713,402

[45] Date of Patent: Dec. 15, 1987

[54] PROCESS FOR PREPARING ANTITHROMBOGENIC/ANTIBIOTIC POLYMERIC PLASTIC MATERIALS

[75] Inventor: Donald D. Solomon, Spring Valley, Ohio

[73] Assignee: Becton, Dickinson and Company, Franklin Lakes, N.J.

[21] Appl. No.: 771,438

[22] Filed: Aug. 30, 1985

[51] Int. Cl.$^4$ .......................... A61K 17/18; B44D 5/12
[52] U.S. Cl. ...................................... 523/112; 514/54; 514/56; 514/822; 604/96; 604/266; 427/2
[58] Field of Search ................... 424/78, 83; 523/112; 525/54.2; 514/56, 54, 822; 604/96, 266; 427/2

[56]       References Cited
       U.S. PATENT DOCUMENTS

| | | | |
|---|---|---|---|
| 3,617,344 | 11/1971 | Leininger et al. | 428/422 |
| 3,846,353 | 11/1974 | Grotta | 117/47 A |
| 4,302,368 | 11/1981 | Dudley et al. | 523/112 |
| 4,442,133 | 4/1984 | Greco et al. | 427/2 |

Primary Examiner—John Kight
Assistant Examiner—Nathan M. Nutter
Attorney, Agent, or Firm—Robert P. Grindle

[57]            ABSTRACT

An antithrombogenic/antibiotic plastic material prepared using an organic solvent system containing a specific chlorofluorocarbon compound and petroleum ether.

14 Claims, No Drawings

PROCESS FOR PREPARING ANTITHROMBOGENIC/ANTIBIOTIC POLYMERIC PLASTIC MATERIALS

BACKGROUND

This invention relates to an antithrombogenic/antibiotic containing plastic material and process for making the same. More particularly, the invention relates to a method for preparing an antithrombogenic/antibiotic plastic material which employs a novel solvent system containing chloroflurocarbon compounds and petroleum ether.

Extensive investigations have been undertaken over many years to find materials that will be biologically and chemically stable towards body fluids. This area of research has become increasingly important with the development of various objects and articles which can be in contact with blood, such as artificial organs, vascular grafts, probes, cannulas, catheters, hyperalimentation catheters and other long indwelling vascular catheters and the like.

Artificial materials are being increasingly used as blood contact devices and may be subject to potential generation of thrombus and bacterial infection. When blood contacts foreign materials a complex series of events occur. These involve protein deposition, cellular adhesion and aggregation, and activation of blood coagulation schemes. Considerable research effort has been focused on this blood-material-interaction in the last twenty years as well as bacterial infection associated with such devices. The overall objective of these investigations has been to minimize the potential for thrombus formation and reduce potential bacterial infection found on the foreign materials, such as the device when introduced into the body upon contact with blood.

Various methods have been devised for producing such a material, most of which involve chemically bonding a quarternary ammonium salt to the polymer and then heparinizing the same. Separately antibiotics have been coupled to these devices using similar techniques. Usually, this is done by incorporating an amine in the polymer, quaternizing the amine, and then heparinizing or bonding an antibiotic to the quarternized material.

In one method taught by R. I. Leininger and G. A. Grode, U.S. Pat. No. 3,457,098, a quaternary amine is incorporated into an epoxy resin. Subsequent exposure to sodium heparinate dissolved in water then results in ionically bound heparin. The polymer systems are essentially epoxy resins which are rigid polymers which are not suitable for forming medical devices such as catheters or other devices requiring extrusion. These polymers also are not appropriate where flexibility in the device is required.

R. I. Leininger and R. D. Falb disclose in U.S. Pat. No. 3,617,344 another process for binding heparin. This system differs from the previous system in that low molecular weight chloromethyl groups are absorbed to the surface of a polymer substrate. Subsequent amination by a tertiary amine and quaternization resulted in a positively charged surface for binding with heparin. The concept, in general, embodies the use of low molecular weight quaternized groups to ionically bind heparin.

U.S. Pat. No. 3,846,353 to H. M. Grotta involves use of long chain alkyl quaternary amines on the surface of a polymer wherein the positively charged surface is exposed to a solution of sodium heparinate. The amines are dissolved in an organic solvent consisting of toluene, petroleum ether and mixtures thereof. The primary deficiency of the Grotta method is the use of toluene as a coating solvent. Toluene, when used with latex materials, results in a swelling of the products and destruction of essential elastic properties, rendering itself practically useless. In particular, this effect is seen with balloons present on balloon catheters wherein the balloon component becomes extremely fragile and is basically destroyed. Additionally, it is known that toluene is carcinogenic. Residues of toluene that may remain on the devices from processing which are targeted for internal use are thus harmful to the ultimate user.

S-P. S. Yen and A. Rembaum prepared a neutral polyurethane elastomer which is subsequently quaternized and ionically bonded to heparin, U.S. Pat. No. 3,853,804. The main disadvantage of this system is that it is a chemical complex and toxic solvents are used to achieve solubility when coating. The coating technique, however, is difficult to perform due to the solvent (DMF) requirement. The patent of N. Harumiya et al., U.S. Pat. No. 3,844,989, describes a polymer composition of waterinsoluble cationic copolymers having hydrophilic components, quarternary amine groups, and hydrophobic moieties. Heparin is bonded ionically to the quaternary ammonium groups via absorption after the polymer components are contacted with a heparin solution. This method involves use of complex synthesis procedures and is not readily applicable to coating other polymeric or non-polymeric materials.

Greco, et al. in U.S. Pat. No. 4,442,133, teaches a method of preparing a surgical vascular graft wherein a length of graft material carries an adsorbed coating of tridodecylmethylammonium chloride (TDMAC) surfactant and an antibiotic bound thereto. A length of graft material such as polytetrafluoroethylene or Dacron is soaked in a 5% benzalkonium chloride solution of TDMAC for 30 minutes at room temperature, air dried and then washed in distilled water to remove excess TDMAC. The use of such aromatic solvents are not fully acceptable because they are alcohol soluble and water swellable and can be more brittle than the long chain alkyl coupling agents.

It would be desirable to provide a material which has excellent biological and chemical stability towards body fluids, namely blood, and which retains its antithrombogenic agent and antibiotic effect for a long term while being slowly leachable when in contact with blood. It would also be desirable to provide materials which, when made, use solvent systems that are safe and non-carcinogenic not only for the manufacturer but also for the ultimate user.

The present invention accomplishes all of these needs by use of a particular organic solvent system containing specific chlorofluorocarbons and petroleum ether. More particularly, the invention involves a method for making an antithrombogenic/antibiotic plastic material, which comprises: exposing the polymeric plastic material to an organic solvent system containing dissolved therein a quaternary ammonium compound, said organic solvent system consisting essentially of (1) a chlorofluorocarbon selected from the group consisting of 1,1,2-trichloro-1,2,2-trifluoroethane; 1,2-difluoro-1,1,2,2-tetracloroethane; 1,1-difluoro-1,2,2,2-tetrachloroethane; and mixtures thereof (2) petroleum ether, wherein the components are present in a parts ratio ranging from 9 to 1 parts chlorofluorocarbon to 1 part petroleum ether; and thereafter exposing said polymeric polymer surface to a solution of a material selected from an antithrombogenic agent, an antibiotic agent or mixtures thereof.

In another embodiment, the present invention relates to devices containing an antithrombogenic/antibiotic material prepared by the novel process of this invention.

The term antithrombogenic agent or material as used herein refers to any material which inhibits thrombus formation on its surface, such as by reducing platelet aggregation, dissolving fibrin, enhancing passivating protein deposition, or inhibiting one or more steps within the coagulation cascade and which form an ionic complex with quaternary ammonium salts. Illustrative antithrombogenic materials may be selected from the group consisting of heparin, prostaglandins, sulfated polysaccharide, and mixtures thereof. Heparin is preferred. It should be understood that these materials are used in their natural form or as salts thereof, such as the sodium, or lithium salt. In addition to the foregoing antithrombogenic agents, optional supplemental amounts of antithrombogenic agents may also be used that are not reactive within the scope of the invention to further enhance the effects of the materials. Exemplary materials include urokinase, streptokinase, albumin and so forth.

The term antibiotic agent or material as used herein refers to any material which inhibits bacterial infection. Illustrative antibiotic materials may be selected from a wide range of material that have a reactive carboxyl functionality. Exemplary materials may be selected from the group consisting of penicillin, oxacillin, ticarcillin, carbenicillin, cephalosporins, cefoxitin, cefazolin, dicloxacillin, cloxacillin, and clavulanic acid (or salt form), and mixtures thereof.

The plastic materials used in the invention as the support structure may be selected from a wide range of polymeric material. The particular formations do not constitute a critical aspect of this invention other than to serve as a support substrate for the antithrombogenic agent/antibiotic agent.

Illustrative plastic materials may be selected from the group consisting of polyethylene, polypropylene, polyurethanes, polyurethane-silicone copolymers, polyurethane-ureas, polycarbonates, silicone rubber, polyesters, nylons, natural rubber, polyvinyl chloride, acrylics, polystyrene, copolymers of polycarbonate and silicone rubber and mixtures thereof. The plastic materials are preferably preformed into the desired shape or structure for the particular application prior to treatment according to the invention. Of significant importance is the ability of the support to adhere with the antithrombogenic/antibiotic agents without becoming deformed when the organic solvent is applied to the substrate.

A particularly preferred family of quaternary ammonium compounds useable in the invention are long chain alkyl quaternary ammonium salts. The salt may have 2 to 4 long chain alkyl groups attached to the nitrogen atom, the alkyl groups having from about 10 to about 30 carbon atoms. The alkyl groups can be like or unlike. The remaining groups may be hydrogen, lower alkyl, aryl and aryl alkyl groups. The ammonium cation is not critical and is preferably chlorine. These compounds are generally obtained by heating together a tertiary amine and an alkylating agent to thereby produce the quaternary ammonium salt by standard techniques well known to the ordinary skilled artisan. Preferred quaternary ammonium compounds are selected from the group consisting of tridodecylmethyl ammonium salts, and tetradodecyl ammonium salts and mixtures thereof. The organic solvent system used to prepare the final material is a critical feature of this invention. The organic solvent system must be able to solubilize the quaternary ammonium compound without solubilizing the plastic material; that is, it must be compatible with the plastic support. The solvent system must be capable of being rapidly removed from the plastic material once exposure to the system is complete. In addition, the system must be noncarcinogenic and be nonswelling when contacting is complete; that is, the solvent must not react with or modify the physical properties of the plastic material. A unique combination of ingredients has been discovered which is able to achieve all of these results. The solvent system is composed of two main ingredients, a chlorofluorocarbon and petroleum ether. It has been found that the chlorofluorocarbon may be selected from the group consisting of 1,1,2-trichloro-1,2,2-trifluoroethane, 1,2-difluoro-1,1,2,2-tetrachloroethane, 1,1-difluoro-1,2,2,2-tetrachloroethane, and mixtures thereof.

Another critical feature of the invention is the ratio of the chlorofluorocarbon to the petroleum ether. It has been found necessary to employ in the organic solvent system at least 50% of the chlorofluorocarbon. Preferably, the chlorofluorocarbon to petroleum ether ratio is employed in a parts ratio ranging from 9 to 1 parts chlorofluorocarbon to 1 part petroleum ether. This ratio has been found suitable to obtain maximum dissolution of the quaternary ammonium chloride and an appropriate amount of ionically complexed material, e.g., antithrombogenic, antibiotic and mixtures thereof. At ratios above 9 parts chlorofluorocarbon, incomplete dissolution occurs rendering the final plastic material unacceptable for the intended purpose.

The amount of quaternary ammonium compound dissolved in the organic solvent system may vary widely and is preferably used in amounts of about 0.25% to about 15% by weight of the organic solvent system. Amounts below or above this range may be useable but have been found not to be preferred. This amount of material includes the use of quaternary ammonium compound alone or when it is prereacted to form a complex with the antithrombogenic agent and/or antibiotic agent. The method for performing this prereaction is considered well known and within the skill of the ordinary artisan.

Once the quaternary ammonium compound is dissolved in the organic solvent system, the plastic material is contacted with the solution such as by exposing the contacting surface to the solution. No particular contacting time is necessary. All that is necessary is that the surface be simply exposed, such as by dip coating or spray coating. The solvent is then removed by simple evaporation at ambient conditions.

After removal of the solvent system the quaternary ammonium compound is contacted with the antithrombogenic material and/or antibiotic. This may be conveniently done by dissolving the active material in water or other appropriate solution and re-expose the plastic material with the solution. Contacting may be performed for 1 to 30 minutes to enable ionic coupling of the active material to the quaternary ammonium compound. Excess solution is removed and the product dried. Drying is performed to remove the solvent without inactivating the antithrombogenic agent and/or antibiotic agent. This may be done in a heated oven at temperatures from 40° to 60° C., or air drying overnight. The manner in which the product is dried is considered well known and within the skill of the ordinary artisan.

As an alternate embodiment, the quaternary ammonium compound is prereacted with the active material; namely, antithrombogenic agent and/or antibiotic material. Once prereacted the ionic complex is dissolved in the organic solvent system described above and the surface of the plastic material exposed to the solution. Solvent evaporation then takes place and the product is ready for use or storage.

The plastic material once prepared has a thin passive coating layer or film of the quaternary ammonium compound which is ionically coupled to the antithrombogenic agent/antibiotic agent. The coating resembles a thin film which enables the active component to be slowly leached from the film. This slow leaching effort inhibits bacterial infection when an antibiotic is used and thrombus formation when an antithrombogenic agent is used, or both.

One particularly preferred plastic material is polyurethane polymers which may contain conventional polyisocyanates, low molecular weight glycols and high molecular weight glycols.

The polyisocyanates useful in the invention in introducing the urethane linkage into the polymer chain may be selected from a wide range of aliphatic, cycloalipathic and aromatic polyisocyanates. Useable diisocyanates may contain noninterfering groups, e.g., aliphatic hydrocarbon radicals such as lower alkyl or other groups, having substantially nonreactive hydrogens as determined by the Zerewitinoff test, J. Am. Chem. Soc. 49,3181 (1927). The diisocyanate often has at least 6 carbon atoms and usually does not have more than about 40 carbon atoms. Diisocyanates of about 8 to 20 atoms in the hydrocarbon group are preferred. Suitable diisocyanates include 2,4-toluene diisocyanate; 2,6-toluene diisocyanate; 1,4-cyclohexane diisocyanate; dicyclohexylmethane 4,4'-diisocyanate; xylene diisocyanate; 1-isocyanate-3-isocyanatomethyl-3,5,5-trimethyl-cyclohexane; hexamethylene diisocyanate; methylcyclohexyl diisocyanate; 2,4,4-trimethylhexyl-methylene diisocyanate, isocyanates such as m-phenylene diisocyanate; mixtures of 2,4- and 2,6 hexamethylene-1,5-diisocyanate; hexahydrotolylene diisocyanate (and isomers), naphtylene-1,5-diisocyanate; 1-methoxyphenyl 2,4-diisocyanate; diphenylmethane 4,4'-diisocyanate; 4,4'biphenylene diisocyanate; 3,3'-dimethoxy-4.4biphenyl diisocyanate; 3,3'dimethyl-4,4'-biphenyl diisocyanate; and 3,3'dimethyl-diphenylmethane-4,4'diisocyanate and mixtures thereof. The aliphatic and alicyclic diisocyanates employed in the process of this invention and the products made therefrom generally exhibit good resistance to the degradative effects of ultraviolet light.

The polyisocyanate compound used to form the prepolymers may contain a portion of polyisocyanates having more than two isocyanate (NCO) groups per molecule providing the urethane polymer compositions are not unduly deleteriously affected. The preferred polyisocyanate is selected from the group consisting of 4,4'-diphenylmethane diisocyanate, toluene diisocyanate, isophorone diisocyanate and methylene bis(4-cyclohexyl) diisocyanate.

The low molecular weight glycols may also be used to prepare the prepolymer which materials may have from 2 to 10 carbon atoms. Exemplary of these glycols are ethylene glycol, diethylene glycol, triethylene glycols, 1,4-butanediol, neopentyl glycol, 1,6-hexanediol, 1,2- and 1,3-propylene glycol, 2,3-butylene glycol, cyclohexane dimethanol (1,4-bis hydroxymethyl cyclohexane), dipropylene glycol, and dibutylene glycol.

The high molecular weight glycols useful in the present invention may be a polyether diol or polyester diol and range in number average molecular weight from about 400 to 3,000 and preferably about 500 to about 2,000. Examples of suitable polyhydric alcohols are ethylene glycol, 1,2- and 1,3-propylene glycol, 1,4- and 2,3-butylene glycol, 1,6-hexane diol, 1,8-octane diol, neopentyl glycol, cyclohexane dimethanol (1,4-bishydroxy methyl cyclohexane), 2-methyl-1,3-propane diol, also diethylene glycol, triethylene glycol, tetraethylene glycol, polyethylene glycols, dipropylene glycol, polypropylene glycols, dibutylene glycol and polybutylene glycols. Polyesters of lactones, for example, $\epsilon$-caprolactone or hydroxy carboxylic acids, for example, $\omega$-hydroxycaproic acid, may also be used. Illustrative polyesters may contain hydroxyl groups, for example, reaction products of polyhydric alcohols reacted with divalent carboxylic acids. It is also possible to use the corresponding polycarboxylic acid anhydrides or corresponding polycarboxylic acid esters of lower alcohols or mixtures thereof, for producing the polyesters. The polycarboxylic acids may be aliphatic, cycloaliphatic, aromatic and/or heterocyclic and may optionally be substituted, for example, by halogen atoms and/or unsaturated. Examples of polycarboxylic acids of this kind include succinic acid, adipic acid, suberic acid, azelaic acid, sebacic acid, phthalic acid, phthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid, optionally in admixture with monomeric fatty acids, terephthalic acid dimethyl ester and terephthalic acid dimethyl ester and terephthalic acid bis-glycol ester.

The polyethers containing at least 2, generally 2 to 8, but preferably 2 to 3 hydroxyl groups used in accordance with the invention are also known per se and are obtained, for example, by polymerizing epoxides, such as ethylene oxide, propylene oxide, butylene oxide, tetrahydrofuran, styrene oxide or epichlorohydrin on their own, for example, in the presence of $BF_3$, or by adding these epoxides, optionally in admixture or in succession, to starter components containing reactive hydrogen atoms, such as water, alcohols, or amines, for example, ethylene glycol, 1,3- or 1,2-propylene glycol, 4,4'-dihydroxy diphenyl propane, aniline, ammonia, ethanolamine or ethylene diamine. The most preferred polyether diols are poly(tetramethylene ether) glycols.

While the preferred polyurethane compositions of the invention are thermoplastic, it has been found possible to employ small amounts of crosslinking agents to the compositions when they are coated onto the support in order to render them thermosetting. Suitable crosslinking agents are discussed above and include the listed diisocyanate compounds.

It should be recognized that the products of this invention are useable in a wide variety of devices designed for contacting body fluids. Exemplary articles which can be in contact with body fluids such as blood, include artificial organs, vascular grafts, probes, cannulas, catheters, hemodialysis tubing, hyperalimentation catheters and other long indwelling vascular catheters, and the like. A particularly preferred application, of the products of the invention is in catheter type devices wherein the active agent is coated on either or both interior and exterior surfaces of the catheter.

As a preferred embodiment, the invention involves the preparation of balloon catheters using the solvent system of this invention. Without being limited hereto, a preferred procedure would involve the following steps: a latex or polyurethane balloon catheter is exposed to a solution of quaternary amineantithrombogenic or antibiotic agent wherein the agent has a concentration of 0.1% to 5% (weight by weight). The quaternary ammonium compound may be selected from tridodecylmethyl ammonium salts, tetradodecyl ammonium salts and tridodecylbenzyl ammonium salts along with the organic solvent system containing (1) a chlorofluorocarbon selected from the group consisting of 1,1,2-trichloro-1,2,2-trifluoroethane; 1,2-difluoro-1,1,2,2-tetrachloroethane; 1,1-difluoro-1,2,2,2-tetrachloroethane, and mixtures thereof; (2) and petroleum ether wherein the components are present in a parts ratio of 9 to 1:1.

The antithrombogenic or antibiotic agent may be present in concentrations ranging from 5% to 60% by weight of the quaternary amine-antithrombogenic/antibiotic complex.

After exposure to the solution the balloon catheter is quickly removed and the solvent is allowed to evaporate at room temperature. The catheters are then packaged and stored for use.

The invention will be further illustrated by the following non-limiting examples. All parts and percentages given throughout the specification are by weight unless otherwise indicated.

EXAMPLE 1

This example describes a procedure for manufacturing catheters which are coated with a TDMAC-heparin coating to impart antithrombogenic properties.

A dried TDMAC-heparin (50.0 g) complex was placed in a sealable bottle and the organic solvent was added to dissolve the complex for coating purposes. The organic solvent was comprised of 1,1,2-trichloro-1,2,2-trifluoroethane and petroleum ether in a 9:1 parts ratio. An appropriate amount of organic solvent (4.0:1) was added to the sealable bottle and agitated until dissolution was complete. The final concentration of the TDMAC-heparin was 1.25% (weight to volume).

The TDMAC-heparin complex solution was then placed in a stainless steel tank. The fully assembled thermodilution catheter with a latex balloon attached was then lowered into the TDMAC-heparin solution until fully immersed and then quickly withdrawn. The catheter was then allowed to stand for at least five minutes to allow for the evaporation of the organic solvent.

A five centimeter length of catheter was cut into one centimeter sections and placed in an empty 10×75 mm culture tube. Activated cephaloplastin (0.1 ml) was then pipeted into the tube and the tube placed in a 37 degree centigrade water bath. After one minute, 0.1 ml of human plasma was added and incubated an additional two minutes. After the incubation period, 0.1 ml of 0.02M $CaCl_2$ was added. The culture tube was removed after 20 seconds and tilted back and forth, in and out of the water bath, until a clot was observed. The activated partial thromboplastin time (APTT) measures the anticoagulant efficacy of the coating. The results are shown in Table I. All results were greater than 1800 seconds, which was an arbitrary cut-off for the experiment. Thus, any sample exhibiting an APTT time of 1800 seconds or more was considered highly effective in reducing clot formation. This was compared to a glass control APTT result of 39.2 seconds and an uncoated catheter of 59.3 seconds.

TABLE I

| Sample | APTT (Seconds) |
| --- | --- |
| TDMAC-heparin coated thermodilution catheter* | >1800 |
| Uncoated thermodilution catheter | 59.3 |
| Glass control | 39.2 |

*Coated using the chlorofluorocarbon solvent system.

EXAMPLE 2

This example describes the presence and detection of toluene residuals in catheters coated with TDMAC-heparin using a commonly employed organic solvent system of 1:1 toluene-petroleum ether.

The TDMAC-heparin (2.0 g) complex as used in Example 1 was placed in a sealable flask and 100 ml of a solvent system containing toluene-petroleum ether (1:1) was added. The mixture was agitated until dissolution of the TDMAC-heparin was complete. The solution was then placed in a graduated cylinder and a 20 cm monolumen catheter was exposed to the solution and quickly withdrawn. The catheter was exposed to ambient air to evaporate any excess solvent for a period of one hour. A 20 cm section of the coated catheter was then cut up into one inch pieces and placed in a sealable bottle with 10 ml of carbon tetrachloride. The test sample was then agitated for a period of at least one hour.

Using a Hewlett Packard model 5830A gas chromatograph with a flame ionization detector, the test sample was analyzed for toluene residuals.

Standards were prepared by pipeting 1.0 ml of toluene into a 50 ml volumetric flask and diluting to the mark with carbon tetrachloride to give a 2.0% solution of toluene. Five milliliters of the latter solution was pipeted into another 50 ml volumetric flask and diluted to the mark with carbon tetrachloride to yield a 0.2% solution. The successive dilutions were repeated twice more to produce a final standard of 0.002%, or 20 ppm toluene.

An injection of 0.5 microliters of the 20 ppm standard was made. This was followed by an injection of a 0.5 microliter injection of the test sample. Both the standard and the test sample were injected at least three times. The amount of toluene present was calculated based on the integrated area of the standard toluene peak compared to the observed test sample peak by commonly known analytical methods. The results are shown in Table II. After one hour at ambient conditions the monolumen catheter had 5,245 micrograms of toluene still present on the catheter.

Another catheter was prepared as previously noted and sterilized. The catheter was then tested as above and the results are found in Table II. These results show that even after sterilization a significant amount of toluene residuals (27 micrograms) were present.

Additional catheters were prepared according to the method of Example 1 in that the same chlorofluorocarbon solvent and the same solution concentration was used. 100 ml of the TDMAC-heparin solution dissolved in the chlorofluorocarbon were placed in a graduated cylinder and the catheters were individually exposed to the solution and then quickly withdrawn. After 15 minutes the samples were treated as above and prepared for analysis. As expected no toluene residuals were present. Data are presented in Table II.

TABLE II

| Sample | Coating Solvent System | Toluene Residuals (ug) |
|---|---|---|
| Unsterilized TDMAC-heparin coated polyurethane | Toluene-petroleum ether | 5,245 |
| Sterilized TDMAC-heparin coated polyurethane | Toluene-petroleum ether | 27 |
| Unsterilized TDMAC-heparin coated polyurethane | Chlorofluorocarbon-petroleum ether | 0 |

EXAMPLE 3

This example compares the fragility of latex balloons which have been coated with a TDMAC-heparin complex using the traditional toluene-petroleum ether (1:1) solvent system and a solvent system of this invention, namely, a chlorofluorocarbon. The compositions of the solvent systems used in this example are the same as those found in examples one and two.

Latex balloons coated with TDMAC-heparin using the solvent systems of examples one and two were allowed to stand for 5 minutes and then were inflated with 1.5 cc of air from a standard plastic syringe. The inflation was maintained for 15 seconds. The balloons were observed to note any decrease in pressure due to leaks or other deficiencies. This experiment was repeated for 25 balloon catheters in each solvent system. The results were recorded as BALLOON DESTROYED (a visible loss in inflation) or BALLOON UNAFFECTED. The results are shown in Table III. The results clearly show the chlorofluorocarbon solvent system to be superior due its non-swelling properties when used to coat latex balloon catheters.

TABLE III

| TDMAC-heparin Coating Solvent | No. of Samples Tested | Percent Balloons Destroyed (%) |
|---|---|---|
| Toluene-petroleum ether | 25 | 56 |
| Chlorofluorocarbon | 25 | 0 |

EXAMPLE 4

This example demonstrates the preparation of a TDMAC-antibiotic coated catheter. TDMAC (1.5 g) was weighed and placed into a sealable bottle together with 50 ml of 1,1,2-trichloro-1,2,2-trifluoroethane and petroleum ether in a 9:1 parts ratio. After complete dissolution monolumen catheters were exposed to the solution and removed quickly. After five minutes, the catheters were placed in a solution of cloxacillin (2.5 g per 50 mls or 5%) and exposed for a period of 30 minutes. After this period they were rinsed in distilled water and let dry at ambient conditions.

A Staphlococcus aureus culture was prepared as follows: A Staphlococcus aureus bactrol disk (ATCC#25923) is placed in 4 ml of trypticase soy broth (TSB) medium and incubated overnight at 37° C. on a continuous wrist-action shaker. A 0.4 ml aliquot of the culture was then transferred into 4 ml of TSB medium. This sample was then incubated for 2-5 hours at 37° C. until the visual turbidity was greater than or equal to the $BaSO_4$ standard (0.5 ml of 1% $BaSO_4$+99.5 ml of 1% $H_2SO_4$).

Samples of the TDMAC-antibiotic coated catheters were tested by preparing petri dishes containing Mueller-Hinton agar (5-6 mm in depth). The bacterial broth suspension was streaked evenly in two planes onto the agar plate using a sterile cotton swab. The seeded agar plates were allowed to stand prior to the introduction of the TDMAC-antibiotic coated TPU catheters for approximately five minutes. The coated catheters were placed firmly into the agar circumferentially about the center of the plate using sterile forceps. The plates were then incubated overnight at 37° C. and checked for a zone of inhibition.

The results are shown in Table IV.

TABLE IV

| Test Material | Zone of Inhibition | (Average, mm ± standard deviation) (SD) |
|---|---|---|
| 0 ug Cloxacillin Control* | No inhibition | |
| 1 ug Cloxacillin Control** | 17.0 ± 0.8 | |
| TDMAC-Cloxacillin coated catheters | 42.0 ± 1.7 | |

*sterile paper disk.
**sterile paper disk impregnated with 1.0 ug of Cloxacillin.
Efficiency of the TDMAC-Cloxacillin coated catheters is clearly shown by the 42.0 mm zone of inhibition.

EXAMPLE 5

This example shows the advantages of this invention when applied to the coating of latex balloons used for thermodilution and similar balloon catheters with TDMAC-heparin. Two centimeter square pieces of latex balloon material (where the average film thickness was 0.0069 inches) were accurately measured and exposed to various solvent combinations. The resultant swelling or non-swelling was recorded. The less the latex swelled the more appropriate the solvent. Each latex piece was exposed to a given solvent or solvent mixture for 15 seconds, removed, and immediately measured. The results are shown in Table V. The chlorofluorocarbon is shown to be superior to all other solvents tested.

TABLE V

| Solvent System | Ratio | Percent Increase in Size or Swelling (%) |
|---|---|---|
| Toluene:petroleum ether | 50:50 | 53.3 |
| 1,1,2-trichloro-1,2,2-trifluoroethane:methylene chloride | 90:10 | 43.3 |
| Amyl alcohol:petroleum ether | 90:10 | 13.3 |
| Ethanol:petroleum ether | 50:50 | 6.7 |
| 1,1,2-trichloro-1,2,2-trifluorethane:petroleum ether | 90:10 | 3.3 |

The invention being thus described, it will be obvious that the same may be varied in many ways. Such variations are not to be regarded as a departure from the spirit or scope of the invention and all such modifications are intended to be included within the scope of the claims.

What is claimed is:

1. A process for producing plastic substrates having antithrombogenic and/or antibiotic properties without dissolving the substrate, characterized by
   (a) providing a dual organic solvent system, said dual organic solvent system comprising
      (1) a chlorofluorocarbon component, said chlorofluorocarbon component being a member selected from the group consisting of 1,1,2-trichloro-1,2,2-trifluoroethane; 1,2-difluoro-1,1,2,2-tetrachloroethane; 1,1-difluoro 1,2,2,2-tetrachloroethane, and mixtures thereof;
      (2) a petroleum ether component; and
      (3) the ratio of said chlorofluorocarbon component to said petroleum ether component being within the range of between about nine parts chlorofluorocarbon to one part petroleum ether and one part chlorofluorocarbon to one part petroleum ether;
   (b) dissolving in said dual organic solvent system from said providing step a pre-formed quaternary ammonium antibiotic and/or antithrombogenic complex;
   (c) immersing a plastic material in said dual organic solvent system containing said quaternary ammonium antibiotic and/or antithrombogenic complex from said dissolving step, said plastic material being non-dissolvable in said organic solvent system;
   (d) removing in a first removing step said plastic material from said immersing step; and
   (e) removing in a second removing step said solvent from said dissolving step;
   (f) thereby providing a passively coated thin layer film of quaternary ammonium antibiotic and/or anticoagulant complex on said plastic surface.

2. The method of claim 1, wherein the antithrombogenic material is selected from the group consisting of heparin, prostaglandins, sulfated polysaccharide, and mixtures thereof.

3. The method of claim 1, wherein the plastic material is not soluble in the same organic solvent used to dissolve the quaternary ammonium compound.

4. The method of claim 1, wherein the quaternary ammonium salt having from 2 to 4 alkyl groups each having from about 10 to 30 carbon atoms.

5. The method of claim 1, wherein the quaternary ammonium compound is selected from the group consisting of tridodecylmethyl ammonium salts, tetradodecyl ammonium salts and tridodecylbenzyl ammonium salts.

6. The method of claim 1, wherein the antibiotic material is selected from the group consisting of penicillin, oxacillin, ticarcillin, carbenicillin, cephalosporins, cefoxitin, cefazolin, dicloxacillin, cloxacillin, and clavulanic acid, and mixtures thereof.

7. The method of claim 1, wherein the plastic is a member of the group consisting of polyethylene, polypropylene, polyurethanes, polyurethane-silicone copolymers, polyurethane-ureas, polycarbonates, silicone rubber, polyesters, nylons, natural rubber, polyvinyl chloride, acrylics, polystryene, a copolymer of polycarbonate and silicone rubber, and mixtures thereof.

8. An antithrombogenic/antibiotic plastic material prepared by exposing a polymeric plastic material to a dual organic solvent system in which the polymeric plastic material is non-soluble; said dual organic solvent system having dissolved therein a pre-formed quaternary ammonium antibiotic and/or antithrombogenic complex, said organic solvent system consisting essentially of (1) a chlorofluorocarbon component, said chlorofluorocarbon component being a member selected from the group consisting of 1,1,2trichloro-1,2,2 trifluoroethane; 1,2-difluoro-1,1,2,2-tetra-chloroethane; 1,1-difluoro 1,2,2,2-tetrachloroethane, and mixtures thereof; and (2) petroleum ether, wherein the ratio of said chlorofluorocarbon component to said petroleum ether being within the range of between about nine parts chlorofluorocarbon to one part petroleum ether and one part chlorofluorocarbon to one part petroleum ether, wherein said plastic material is exposed to said dual solvent system for a time sufficient to form a thin film of said complex on the surface of said plastic material, and wherein said dual solvent system is removed from said formed thin film.

9. The plastic material of claim 8 wherein the antithrombogenic material is selected from the group consisting of heparin, prostaglandins, sulfated polysaccharide, and mixtures thereof.

10. The plastic material of claim 8 wherein the quaternary ammonium compound is a long-chain alkyl quaternary ammonium salt having from 2 to 4 alkyl groups each having from about 10 to about 30 carbon atoms.

11. The plastic material of claim 8 wherein the quaternary ammonium compound is selected from the group consisting of tridodecylmethyl ammonium salts, tetradodecyl ammonium salts and tridodecylbenzyl ammonium salts.

12. The plastic material of claim 8 wherein the antibiotic material is selected from the group consisting of penicillin, oxacillin, ticarcillin, carbenicillin, cephalosporins, cefoxitin, cefazolin, dicloxacillin, cloxacillin, and clavulanic acid, and mixtures thereof.

13. The plastic material of claim 8 wherein the plastic is a member of the group consisting of polyethylene, polypropylene, polyurethanes, polyurethanesilicone copolymers, polyurethane-ureas, polycarbonates, silicone rubber, polyester, nylons, natural rubber, polyvinyl chloride, acrylics, polystyrene, a copolymer of polycarbonate and silicone rubber, and mixtures thereof.

14. The plastic material of claim 8 for use in making balloon catheters.

* * * * *